(12) United States Patent
Truckai et al.

(10) Patent No.: US 12,185,978 B2
(45) Date of Patent: Jan. 7, 2025

(54) SURGICAL SYSTEM AND METHOD OF USE

(71) Applicant: Hermes Innovations, LLC, San Jose, CA (US)

(72) Inventors: Csaba Truckai, San Jose, CA (US); John H. Shadduck, San Jose, CA (US)

(73) Assignee: Hermes Innovations, LLC, San Jose, CA (US)

( * ) Notice: Subject to any disclaimer, the term of this patent is extended or adjusted under 35 U.S.C. 154(b) by 0 days.

(21) Appl. No.: 18/353,782

(22) Filed: Jul. 17, 2023

(65) Prior Publication Data

US 2024/0016520 A1   Jan. 18, 2024

Related U.S. Application Data

(63) Continuation-in-part of application No. 15/203,685, filed on Jul. 6, 2016.

(60) Provisional application No. 62/189,008, filed on Jul. 6, 2015.

(51) Int. Cl.
| | | |
|---|---|---|
| *A61B 17/42* | (2006.01) | |
| *A61B 17/00* | (2006.01) | |
| *A61B 17/32* | (2006.01) | |

(52) U.S. Cl.
CPC ............... *A61B 17/4241* (2013.01); *A61B 2017/00039* (2013.01); *A61B 2017/00123* (2013.01); *A61B 17/32002* (2013.01); *A61B 2017/4216* (2013.01)

(58) Field of Classification Search
CPC .............. A61B 17/4241; A61B 2017/00022
See application file for complete search history.

(56) References Cited

U.S. PATENT DOCUMENTS

| | | |
|---|---|---|
| 5,868,673 A | 2/1999 | Vesely |
| 7,018,391 B2 | 3/2006 | Spitz et al. |
| 7,172,603 B2 | 2/2007 | Burbank et al. |
| 8,974,450 B2 | 3/2015 | Brannan |
| 9,044,210 B1 | 6/2015 | Hoyte et al. |
| 2004/0082850 A1 | 4/2004 | Bonner et al. |
| 2006/0200123 A1 | 9/2006 | Ryan |
| 2008/0281309 A1 | 11/2008 | Dunning et al. |
| 2010/0081964 A1 | 4/2010 | Mark et al. |
| 2010/0152756 A1 | 6/2010 | Mark |
| 2012/0123400 A1 | 5/2012 | Francischelli et al. |
| 2013/0131457 A1* | 5/2013 | Seckin ............... A61B 17/4241 600/235 |
| 2013/0172870 A1 | 7/2013 | Germain et al. |
| 2014/0031817 A1 | 1/2014 | Totman et al. |
| 2014/0276839 A1 | 9/2014 | Forman et al. |
| 2014/0336643 A1 | 11/2014 | OrczyTimko et al. |
| 2016/0220314 A1* | 8/2016 | Huelman ............... A61B 34/20 |
| 2017/0056055 A1 | 3/2017 | Truckai |

(Continued)

FOREIGN PATENT DOCUMENTS

| | | |
|---|---|---|
| CN | 102149334 | 8/2011 |
| WO | WO 2001/008578 | 2/2001 |

(Continued)

*Primary Examiner* — Alyssa M Alter
*Assistant Examiner* — Jessandra F Hough
(74) *Attorney, Agent, or Firm* — Levine Bagade Han LLP

(57) ABSTRACT

Systems and devices for resecting and removing tissue or organs from the interior of a patient's body, in a minimally invasive laparoscopic procedure while preventing any dispersion of potentially malignant tissue during the resection process.

21 Claims, 21 Drawing Sheets

(56) References Cited

U.S. PATENT DOCUMENTS

2020/0253639 A1*  8/2020  Kim .................. A61B 17/29
2023/0077141 A1*  3/2023  Scheib ................ A61G 13/101

FOREIGN PATENT DOCUMENTS

| WO | WO 2010/039316 | 4/2010 |
| WO | WO 2014/004051 | 1/2014 |
| WO | WO 2014/013491 | 1/2014 |
| WO | WO 2017/007851 | 1/2017 |

\* cited by examiner

SURGICAL SYSTEM AND METHOD OF USE

RELATED APPLICATIONS

This application is a Continuation-in-Part of U.S. application Ser. No. 15/203,685 filed on Jul. 6, 2016, which is a non-provisional of U.S. Provisional Patent Application No. 62/189,008, filed on Jul. 6, 2015, the content of each of which are incorporated herein by reference.

FIELD OF THE INVENTION

The present invention relates to systems and devices for resecting and removing tissue or organs from the interior of a patient's body in a minimally invasive laparoscopic procedure while preventing any dispersion of potentially malignant tissue during the resection process.

BACKGROUND

Several surgical procedures require removing a tissue mass or an organ from the body of a patient in an efficient manner preventing dispersion of potentially malignant tissue during the resection process. One such procedure is a hysterectomy, where a woman's uterus is detached and removed from her body. Hysterectomy is typically performed in cases of severe endometriosis, the presence of fibroids, cancer, cervical dysplasia, uterine prolapse, and more. With the advent of minimally invasive surgery such as laparoscopic surgery, large tissue masses such as the uterus are removed through small incisions, decreasing post operative pain and hospitalization time.

Several types of hysterectomy are performed fully or partially laparoscopically, and these include Total Laparoscopic Hysterectomy (TLH), where the uterus and cervix are removed through a few small incisions made in the abdomen; Laparoscopic Supracervical Hysterectomy (LSH) where the uterus is removed, but the cervix is left intact. In both cases, the uterus is removed through one of the small incisions using an instrument called a morcellator. Another approach is a Total Vaginal Hysterectomy (TVH), where the uterus and\or cervix are removed through the vagina.

In laparoscopic hysterectomies, for example, the uterus is removed using instruments inserted through small tubes into the abdomen, resulting in a few small incisions in the abdomen. A laparoscopic approach offers surgeons better visualization of affected structures (e.g., by using an endoscope) than either vaginal or abdominal hysterectomy.

There remains a need to resect and/or remove tissue from the interior of an organ while maintaining a surface of the organ to prevent tissue from being removed from spreading within the body. Such procedures and devices require an ability for the medical practitioner to be aware of the position of the cutting device relative to the surface of the tissue of the organ while the device is within the organ. This would allow the physician to remove a significant portion of the tissue within the organ and remove the organ from the body. Such devices and systems can be used in any part of the body, with a hysterectomy being one example.

SUMMARY

The present disclosure includes systems and methods for resecting and/or removing tissue from the interior of an organ and monitoring a proximity of the tissue removal device to a surface of the organ to prevent the surface of the organ from being cut or breached by the cutting device. In some variations, the cutting device advances through the outer surface of the organ when inserted into a cavity within the organ. In alternate variations, the device is introduced through an opening of the organ. The devices and methods described herein are explained with respect to performing a hysterectomy. However, the methods, devices, and systems can be used in any body location unless otherwise specifically claimed.

In one example, the prevent disclosure teaches a system for resecting tissue within an interior of an organ. Such a variation can include a probe having a proximal portion and a distal portion; a cutting member configured to remove tissue and located at the distal portion of the probe; at least one sensor located adjacent to the cutting member, the sensor configured to generate a signal comprising an environmental condition adjacent to the cutting member; and a controller configured to receive the signal of the environmental signal and use the signal to determine whether the cutting member is adjacent to an exterior surface of the organ.

The sensor can comprise a mechanism selected from a group consisting of: a capacitance sensing mechanism, an impedance sensing mechanism, an optical sensing mechanism, and an ultrasound mechanism.

In one variation of the system, the controller is configured to generate an alert signal upon detecting that the cutting member is adjacent to the exterior surface of the organ. Such an alert signal can comprise an aural alert, a visible alert, a tactile alert, and a combination thereof.

The probe and cutting mechanism can comprise a mechanical or an electrosurgical based cutting mechanism. In certain variations, the sensor is located adjacent to the cutting mechanism or adjacent to a window or opening in the probe that exposes the cutting member.

In variations where the cutting mechanism comprises an electrosurgical cutting mechanism, the cutter can comprise an electrode element, a resistively heated element, an inductively heated element, an ultrasound transmission element, and a light energy transmission element.

The controller of the present system can include an algorithm for de-activating the cutting member in response to the signal that the cutting member is within a predetermined proximity to the organ surface. The algorithm can also modulate the speed that the cutting member removes tissue.

The systems described herein can further comprise a negative pressure source in fluid communication with the probe and cutting mechanism, where the negative pressure source extracts resected tissue through a passageway in the probe. Alternatively or in combination, the systems can comprise a positive pressure source in fluid communication with the probe.

The present disclosure also includes methods for resecting tissue. In one such variation, the method can comprise introducing a probe into an interior of an organ, wherein a working end of the probe includes a cutter and sensor mechanism adjacent to the cutter, where the sensor mechanism is configured to detect a surface of the organ; resecting tissue with the cutter generating a signal with the sensor mechanism when the sensor mechanism detects the cutter approaching the organ surface from the interior of the organ; and removing a substantial volume of the organ from within the interior of the organ without the cutter perforating the organ surface from the interior thereby preventing dispersion of potentially malignant tissue.

The method can further include variations where the sensor mechanism comprises at least one of a capacitance sensing mechanism, an impedance sensing mechanism, an optical sensing mechanism, and an ultrasound mechanism. In an additional variation, the sensor mechanism is operatively coupled to a controller to provide signals consisting of at least one of aural, visible or tactile signal.

The method can also include a controller that employs an algorithm for de-activating the cutter in response to a signal that the cutter is within a predetermined proximity to the organ surface. The de-activating step can comprise stopping movement of the cutter or stopping energy delivery to the cutter. In additional variations, the controller includes an algorithm for modulating the speed of movement of the cutter in response to the signal that the cutter is within a predetermined proximity to the organ surface.

Variations of the method can also include mobilizing the organ with the intact organ surface after the substantial volume is removed and removing the organ from the patient's body.

In an additional variation, a method of resecting tissue comprises introducing a probe into an interior of an organ, wherein a probe working end includes a first sensor component; disposing a second sensor component at an exterior surface of the organ; and activating the probe to resect tissue wherein the first and second sensor components cooperate to provide at least one signal indicating a proximity of the probe to the exterior surface of the organ. At least one of the sensor components comprises a component selected from the group consisting of a capacitance sensing mechanism, an impedance sensing mechanism, an optical sensing mechanism, and an ultrasound mechanism and the other sensor component cooperates to enhance a sensitivity of said signals.

The sensor component can include a gas, liquid, or gel disposed at the exterior of the organ. Alternatively, or in combination, the second sensor component comprises a sac disposed at the exterior of the organ.

In an additional variation, the present disclosure includes a method for laparoscopic hysterectomy. For example, the method can include introducing a probe into a uterine cavity, wherein a probe working end includes a sensor mechanism for sensing the proximity of the cutter to an exterior surface of a uterine wall; activating the probe to resect tissue from within the uterine cavity wherein the sensor mechanism provides signals indicating the proximity of the cutter to said exterior surface; and removing a substantial volume of the tissue from within the uterine cavity without perforating the uterine wall thereby preventing dispersion of potentially malignant uterine tissue. The method can also include the step of sealing and/or ligating blood vessels communicating with the uterus.

The method can further comprise removing a substantial volume of the tissue within the uterine cavity without perforating the uterine wall from within the cavity such that the uterine wall forms an intact shell. The method can also include transecting the shell of the uterine wall away from the patient's body.

The methods and/or devices described herein can be performed in a supracervical procedure, a trans-vaginal approach, an endoscopic approach, or in an open surgical approach.

In an additional variation, a method of resecting at least a portion of an organ can include isolating the tissue mass or organ from its blood supply; introducing a resecting probe into the organ, wherein a probe working end includes a cutter and sensor mechanism for sensing the proximity of the cutter to a surface of the organ; activating the cutter to resect tissue wherein the sensor mechanism provides signals indicating the proximity of the cutter to the organ surface; and removing a substantial volume of the organ without perforating the organ surface thereby preventing dispersion of potentially malignant tissue.

BRIEF DESCRIPTION OF THE DRAWINGS

The disclosed variations will next be described in greater detail by reference to exemplary embodiments that are illustrated in the drawings.

DETAILED DESCRIPTION OF THE INVENTION

Figure 1:
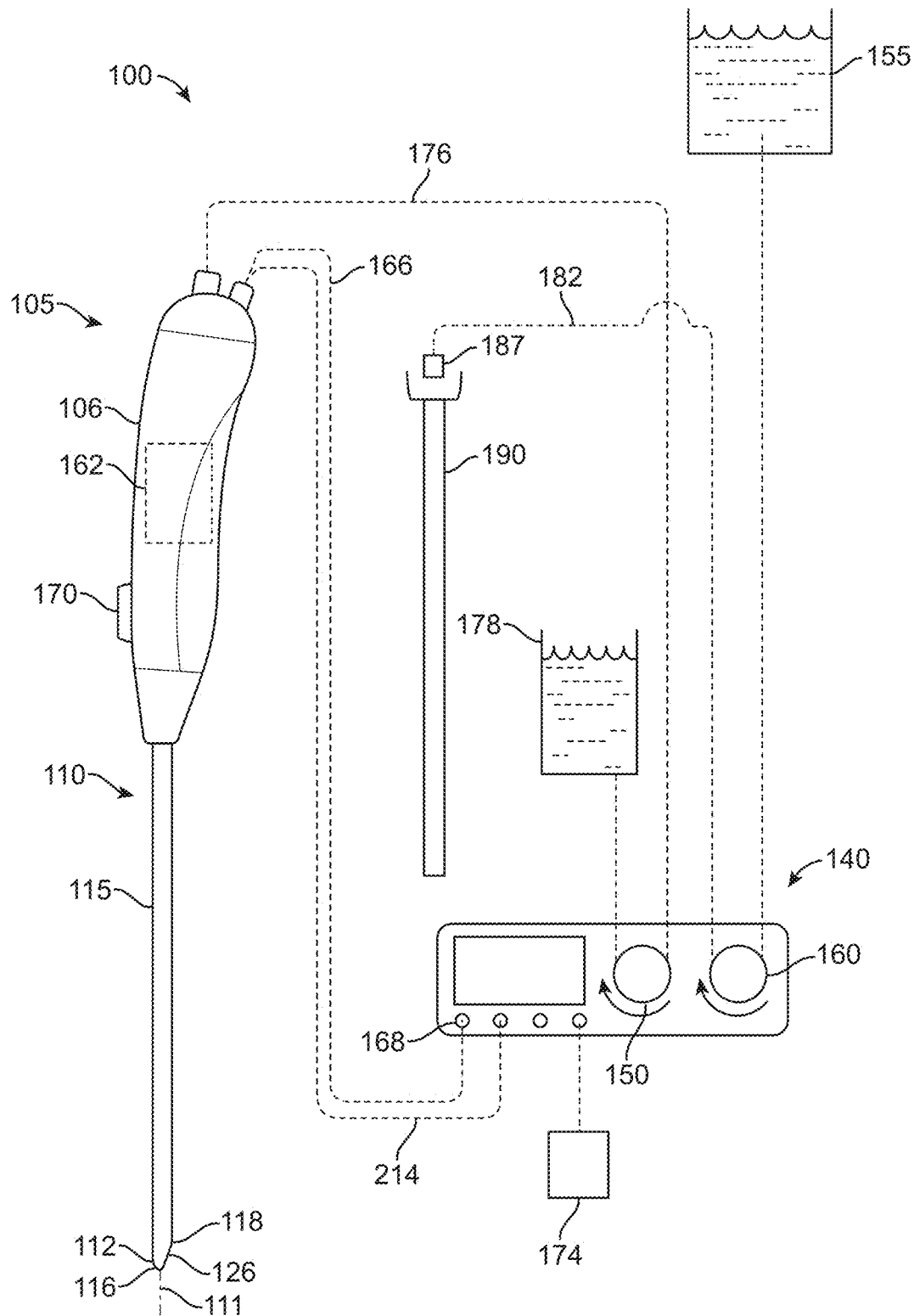
FIG. 1 is a schematic view of a tissue resection device and a block diagram of operating components corresponding to the invention for use in a laparoscopic resection procedure.
Figure 2:
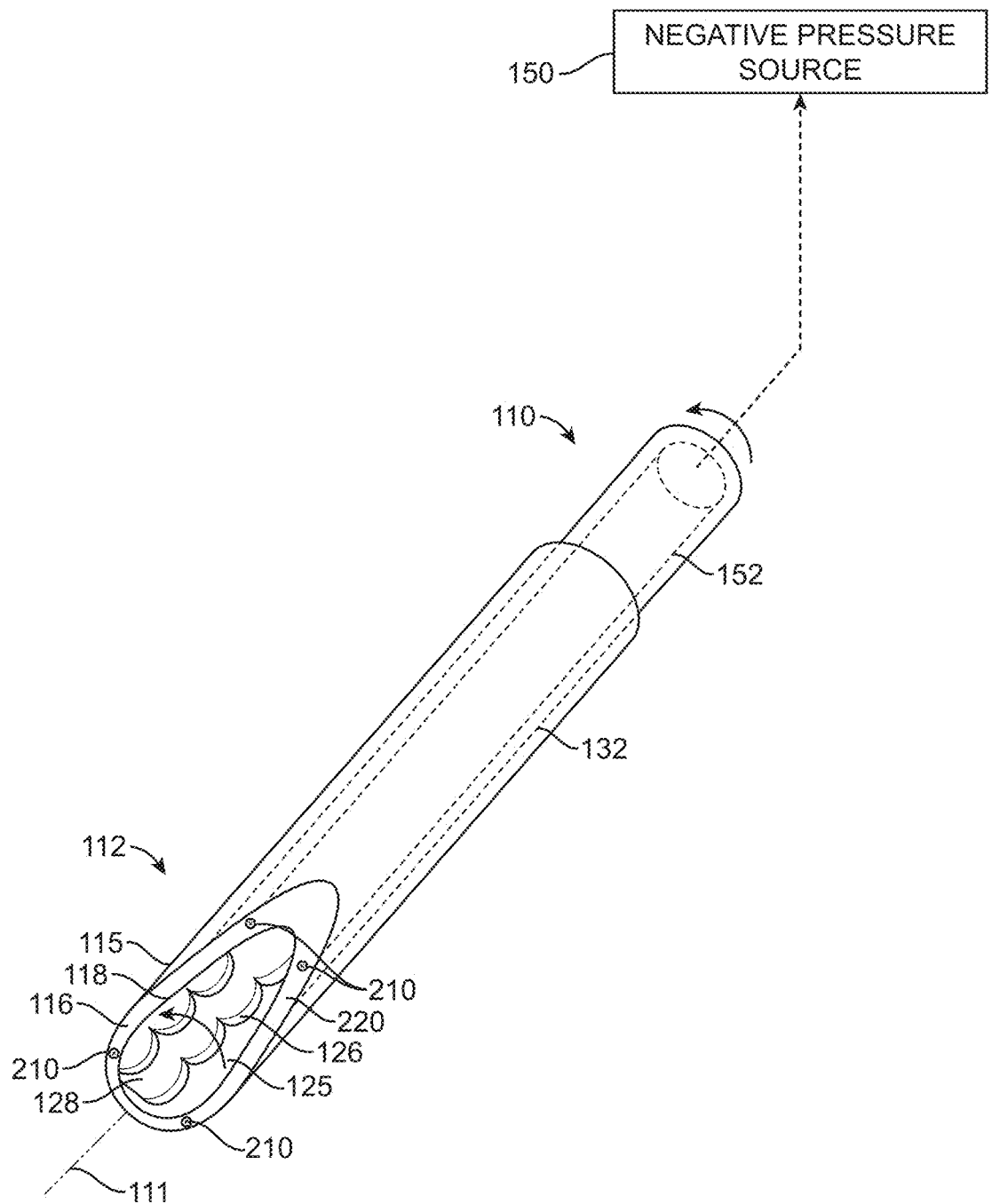
FIG. 2 is a perspective view of the working end of a resection device of the type shown in FIG. 1, showing a sensor mechanism carried by the working end.

FIGS. 1 and 2 illustrate a tissue resection system 100 that includes a hand-held single-use tissue cutting device or resection device 105. The device 105 has a handle portion 106 that is coupled to a shaft portion 110, having an outer diameter ranging from about 3 mm to 20 mm. The shaft portion 110 extends along axis 111 and can have a length suitable for introducing directly into a body space or into an organ, for example, introducing through a trocar in a laparoscopic procedure or for introducing through a working channel of an endoscope.

In one variation, a hand-held resecting device 105 as depicted in FIGS. 1 and 2 can be used to perform a laparoscopic hysterectomy procedure as depicted in FIGS. 3A to 3D. Referring to FIGS. 1 and 2, the resection device 105 is a tubular cutter as is known in the art with a shaft portion 110 and working end 112. The shaft 110 comprises an assembly of a first or outer sleeve 115 extending along axis 111 to a distal end 116, having a window 118 therein for receiving tissue. A second or inner sleeve 125 with a distal blade edge 126 and distal opening 128 is dimensioned to rotate in bore 132 of outer sleeve 115. The outer and inner sleeves, 115 and 125, can be fabricated of thin-wall stainless steel, but any other suitable materials can be used. As can be understood from FIGS. 1-2, rotation of the inner sleeve 125 will cut tissue captured in the window 118 of the outer sleeve. FIG. 2 shows the working end 112 of the assembly of outer sleeve 115 and inner sleeve 125 with the inner sleeve 125 rotating and in a partially window-open position.

As can be seen in FIG. 1-2, the resection system 100 can include a controller 140 that is adapted for (i) controlling a motor drive in the resecting device 105 as will be described below; (ii) controlling at least one sensor system carried by the resection device 105 that will be described further below, (iii) controlling a negative pressure source or outflow pump 150 operatively coupled to a tissue extraction channel 152 in the resection device 105, and (iv) controlling an optional fluid source 155 and inflow pump 160 for distending or flooding a treatment site with a fluid, such as saline.

Referring FIG. 1, the controller 140 includes algorithms for driving a motor 162 in the handle 106 of the resecting device 105. The motor can be a brushless DC motor and controller 140 can be configured to operate the motor at a preset RPM or a user-selected RPM between 100 and 2,000 RPM. FIG. 1 shows an electrical cable 166 extending from connector 168 in the controller 140 to the resecting device handle 106. The resecting device 105 can be operated by a switch 170 in the handle 106 or a footswitch indicated that 174 coupled to the controller 140.

Still referring to FIG. 1, the controller 140 includes a roller pump 150 that provides a negative pressure source for extracting tissue through the passageway 152 in the resecting device 105. The roller pump 150, in combination with the flexible tubing 176, is configured to pump fluid and extracted tissue chips through the tubing into the collection reservoir 178.

Again referring to FIG. 1, controller 140 can have a second roller pump 160 adapted to provide fluid flows into a site targeted for resection. A fluid source 155 is coupled to a flexible fluid infusion tubing 182 that is engaged by the roller pump 160 and that further extends to a fitting 187 on cannula 190, which is adapted for access to the treatment site. The cannula 190 can be inserted into the site and can be used as an access pathway for the resection device 105, or the cannula can be used for fluid infusion independent of the resection device. In another variation, the fluid infusion tubing 182 can be coupled to the resection device 105 so that fluid flows to the working end 112 and window 118 in a path in the annular space between the outer sleeve 115 and the inner sleeve 125.

Now turning to FIG. 2, the working end 112 of the resecting device 105 is shown in an enlarged perspective view. In one variation shown in FIG. 2, a sensor system is shown disposed around the cutting window 118 in the working end. This variation shows four capacitance sensors 210 disposed around the window 118, which comprise the distal termination of paired wire leads as is known in the art capacitance sensors. The capacitance sensors 210 are coupled to the controller 140 through cable 214 (FIG. 1). The sensors 210 can be carried in a thin polymeric coating 220 on the outer sleeve 125. In this embodiment, there are four capacitance sensors, but there could be from 1 to 20 sensors on the outer sleeve 125. In another variation, one or more capacitance sensors could be carried on the inner sleeve surface opposing the sharp blade edges. As will be described below, capacitive sensors 210 can provide a signal to the user when the cutting blade 126 (FIG. 2) approaches the periphery of an organ targeted for resection. While FIG. 2 shows a variation of the resecting device 105 with capacitance sensors 210, it should be appreciated that other types of sensors can be used to determine the proximity of the cutting blade to an organ periphery, such as optical sensors, impedance sensors, magnetic sensors and the like.

Figure 3A:
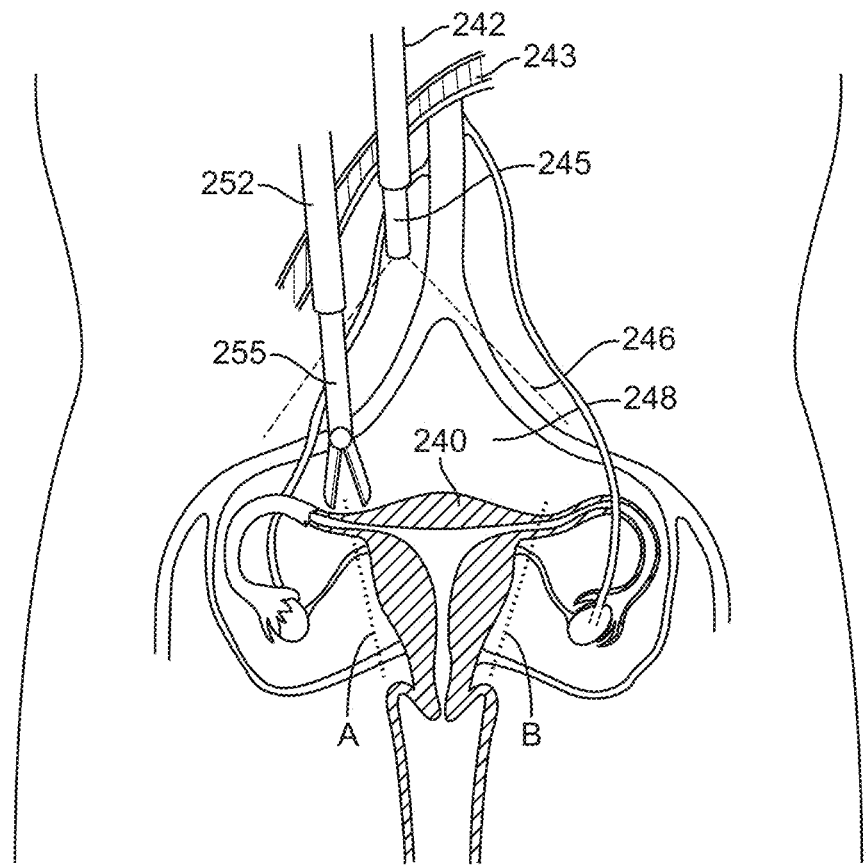
FIG. 3A is a schematic view of the patient's uterus and abdominal region showing the initial steps of a laparoscopic hysterectomy procedure with an ultrasound component de-coupled from a resection device. The ultrasound component can optionally include a plurality of piezoelectric elements carried therein.

Now turning to FIGS. 3A to 3D, a method corresponding to the invention is described relating to the resection of a uterus in a new form of laparoscopic hysterectomy. FIG. 3A is a schematic view of the patient's abdominal cavity and a uterus 240 targeted for resection. In a first step of the method, a first sleeve or cannula 242 is introduced through the abdominal wall 243, and an endoscope 245 is inserted through the sleeve to provide a field of view 246 in the abdominal cavity 248.

FIG. 3A further shows a second cannula 252 introduced through the abdominal wall 243, after which a cutting-sealing device 255, such as electrosurgical cutting and sealing device, is introduced through the cannula 252 for use in sealing and transecting blood vessels communicating with the uterus 240. As is known in the art of performing a laparoscopic hysterectomy, the uterine arteries are sealed and transected, and the broad ligaments, fallopian tubes, and fascia are transected along lines A and B to mobilize the uterus 240. Thereafter, the cutting-sealing device 255 is withdrawn from cannula 252.

Figure 3B:
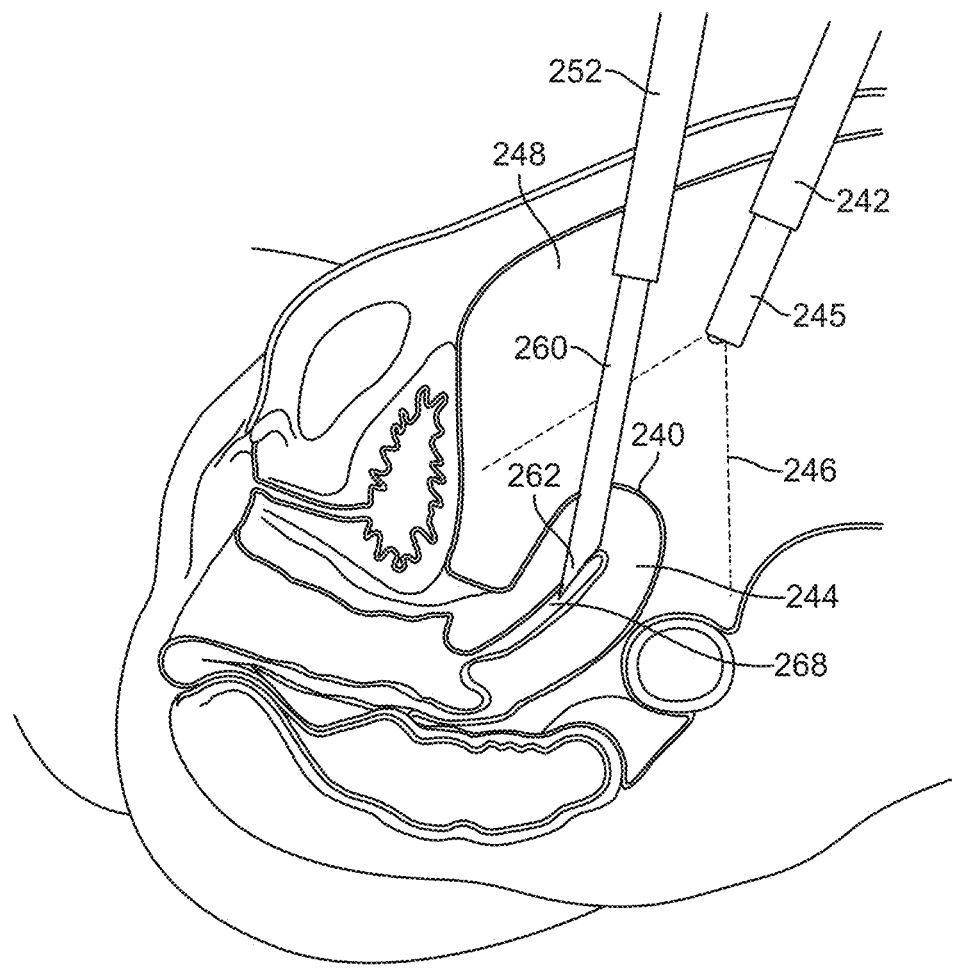
FIG. 3B is a sagittal view of the patient's uterus and abdominal cavity, showing another step comprising introducing a trocar through the uterine wall from the abdominal cavity.

FIG. 3B depicts a subsequent step of the method wherein a sharp trocar sleeve 260 is introduced through the second cannula 252 by the physician, and then, under laparoscopic vision, the distal tip 262 of the trocar sleeve 260 is advanced through the uterine wall 244 into the uterine cavity 268.

Figure 3C:
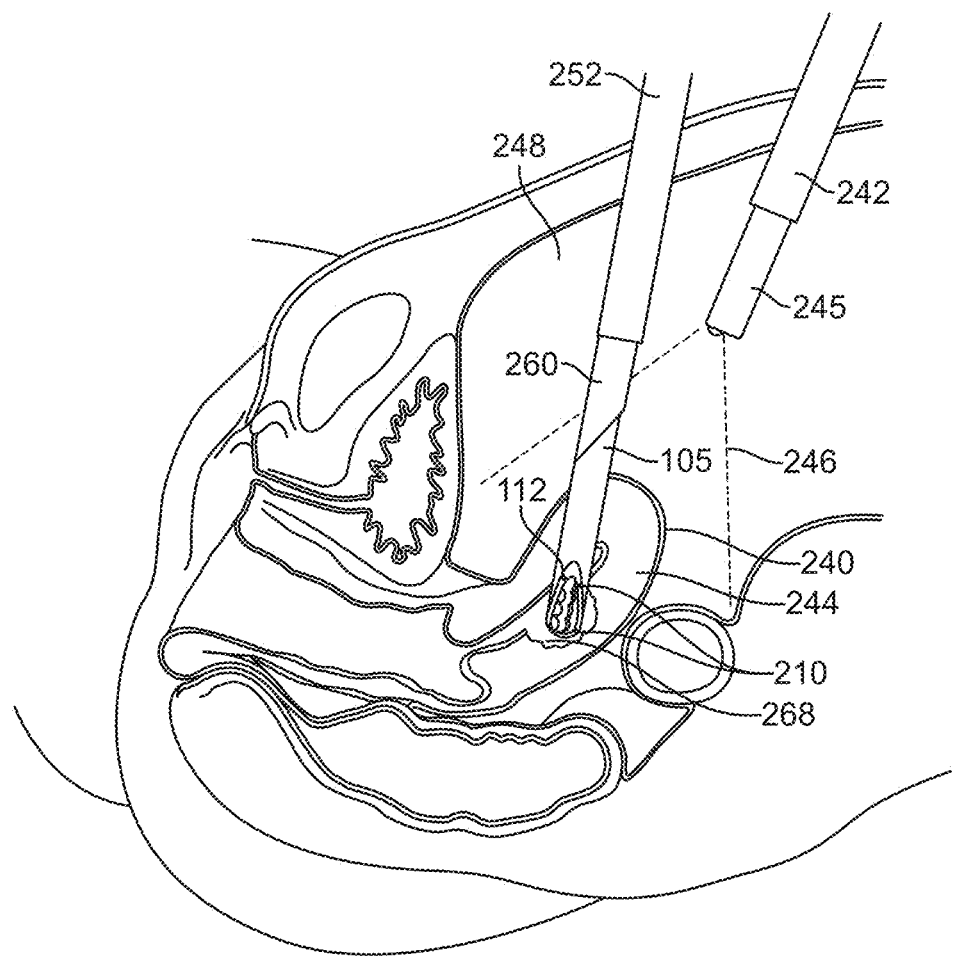
FIG. 3C is a sagittal view of a step comprising introducing the resecting device into the interior of the uterus, actuating the device to reset tissue, and removing tissue through the passageway in the resecting device.

FIG. 3C shows the next step in the method wherein the resection device 105 is introduced through the cannula 252 and trocar sleeve 260 into the interior of the uterus 240, and thereafter the trocar sleeve 260 is withdrawn, leaving the working end 112 of the resection device 105 within the interior of uterus 240. In one variation of the method, the fluid source 155 and infusion tubing 182 are coupled to the resection device 105 to provide a fluid flow into the uterine cavity 268 through the annular space between the outer sleeve 115 and the inner sleeve 125 (see FIGS. 1-2). By this means, the uterine cavity 268 can be distended to some extent, while the controlled fluid inflow assists in the resecting procedure and further assists in the extraction of tissue debris from the site. In another variation (not shown), a cervical seal member can be introduced trans-vaginally to seal the uterine cavity 268, wherein the cervical seal can be a probe shaft, an inflatable member, or other types of seals known in the art. In another variation, the fluid source 155 and infusion tubing 182 can be coupled to a trans-cervical probe and seal (not shown) to provide a fluid flow into the uterine cavity 268.

Figure 3D:
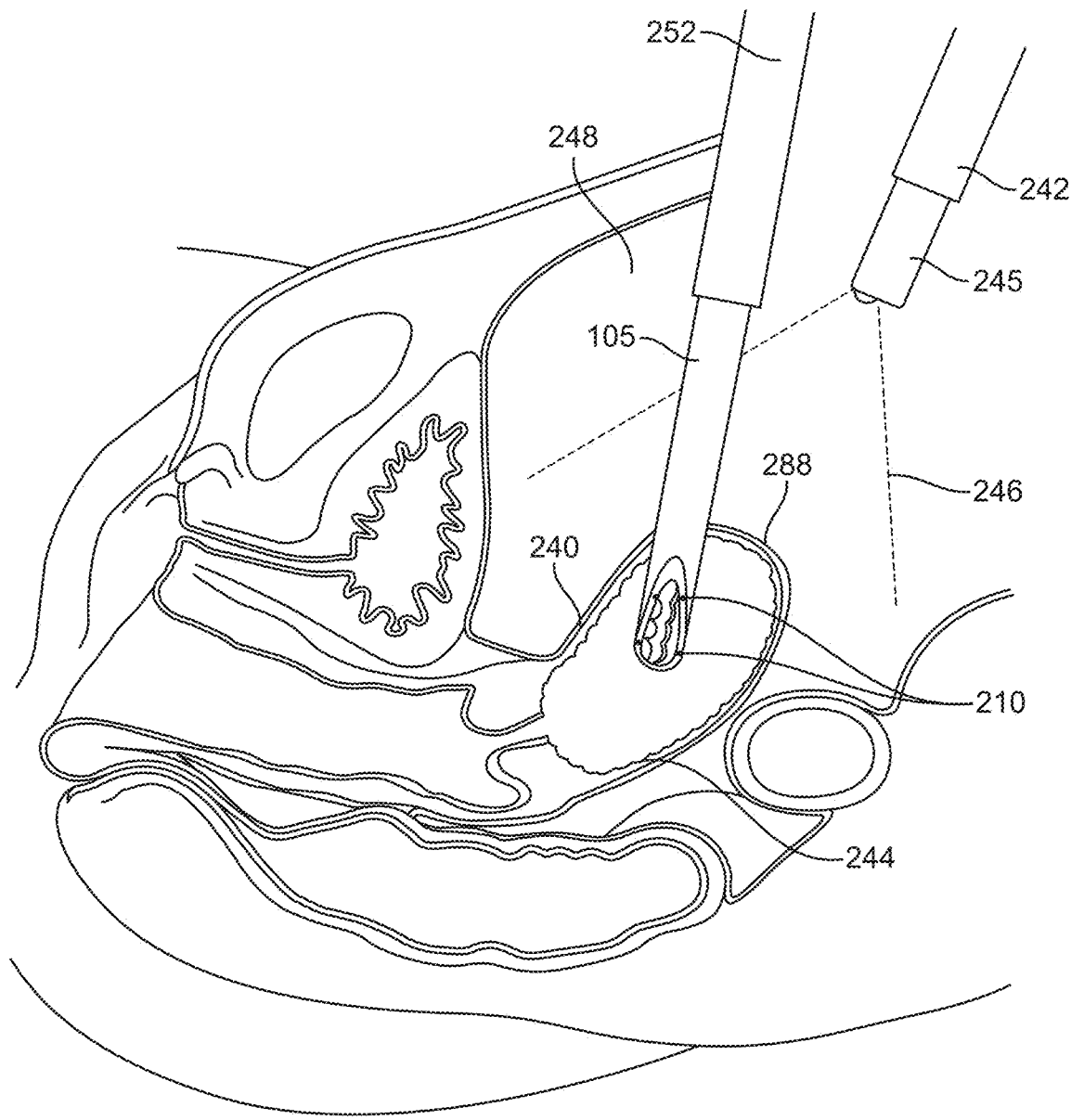
FIG. 3D is a sagittal view of a further step comprising introducing utilizing the resecting device to reset and remove a substantial volume of the interior of the uterus while sensor mechanisms indicate and/or control when a cutting member comes into proximity to the wall of the uterus.

Still referring to FIG. 3C, the physician then can actuate the resecting device 105 to resect tissue in a blind method while observing the exterior of the uterus 240 with the endoscope 245. The physician can manipulate the working end 112 of the resecting device 105 to core out the interior of the uterus 240 while leaving the uterine wall 244 completely intact as it cores tissue from within and apart from any access openings. It can now be seen that the purpose of the capacitance sensors 210 is to provide signals to indicate the proximity of the cutting blade 126 to the exterior of the uterine wall 244. As indicated in FIG. 3D, in one variation, the capacitance sensors 210 can sense a change in tissue capacitance when the window 118 and blade move close to the exterior of the uterine wall 244. The plurality of capacitive sensors 210, as shown in FIG. 2, allows for sensing proximity to the surface of the uterine wall no matter the orientation of the working end 112. The resecting procedure can be considered complete when the physician has removed a substantial volume of tissue from the interior of the uterus 240 and, in effect, leaves only a shell 288 of the uterus in place, as shown in FIG. 3D. By this means, it can be understood that no resected tissue, and thus no potentially malignant tissue, has been exposed outside of the interior of uterus 240. Rather, all tissue has been resected and immediately extracted through passageway 152 in the inner sleeve 125 and then collected in the collection chamber 178 with no possibility of contaminating the abdominal cavity 248. In one aspect of the method, at least 50%, at least 60%, at least 70%, at least 80%, or at least 90% of the mass of the uterus 240 is resected and extracted to leave a reduced-volume shell 288 of the uterus (FIG. 3D). Following the resection and extraction of the bulk of the uterus 240, the reduced-volume shell 288 of the uterus can be removed in methods known as in a conventional supracervical or other laparoscopic hysterectomy procedure. Typically, the reduced-volume uterine shell 288 can be removed intact in a transvaginal approach.

During the resection steps described above, the controller 140 can modulate fluid inflows to and from the site by controlling the roller pumps. The flow rates into and out of the uterine cavity 268 can be from 10 mL/min to 1000 mL/min and also can be modulated depending on a cutting speed selected by the physician.

Figure 4:
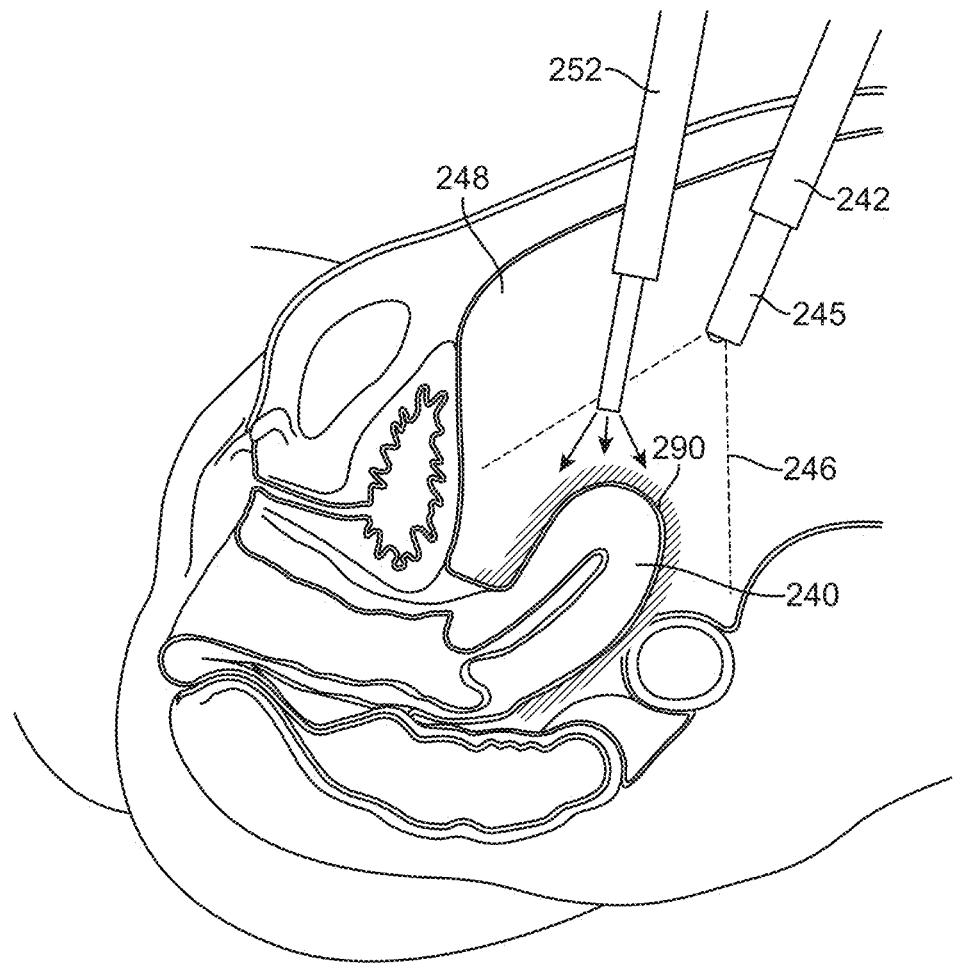
FIG. 4 is a sagittal view of the patient's uterus, and abdominal cavity showing the variation in the method wherein a sensor responsive media is applied around the exterior surface of the uterus.
Figure 5:
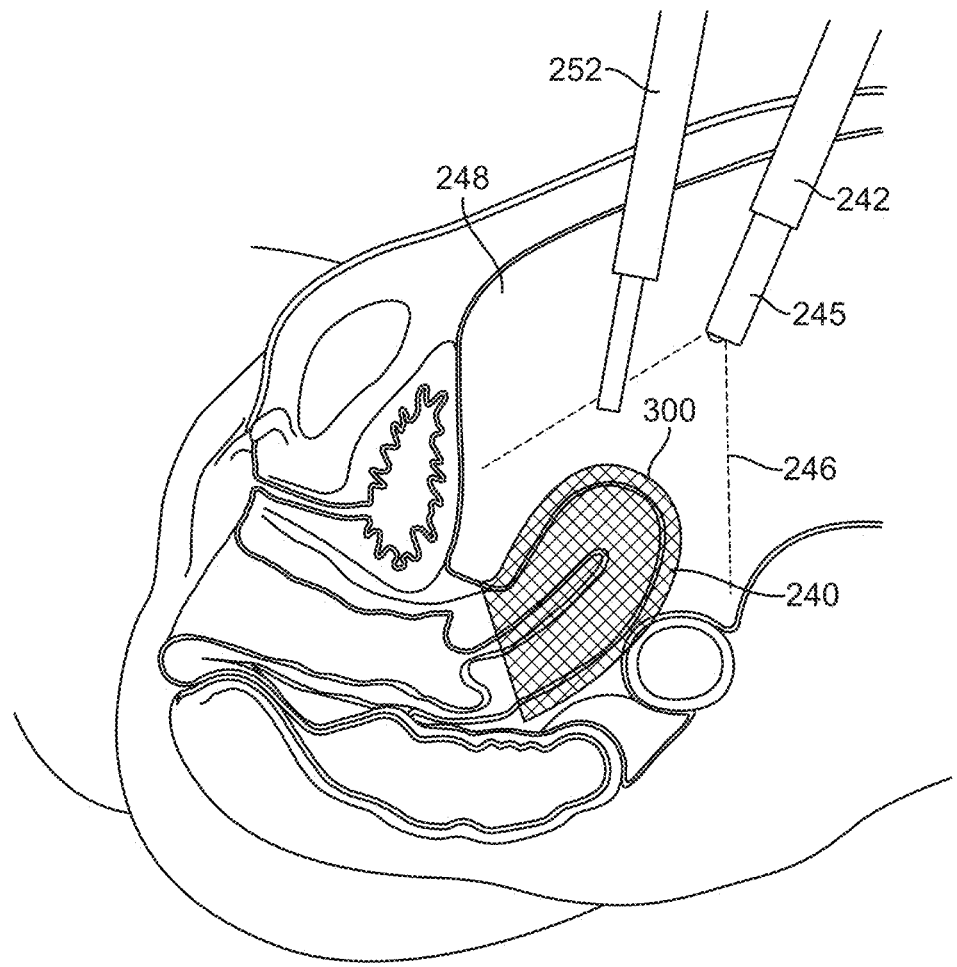
FIG. 5 is another sagittal view of the patient's uterus and abdominal cavity, showing another variation in the method wherein a sensor responsive mesh sac is disposed around the exterior surface of the uterus.

In another embodiment in another variation shown in FIG. 4, a sensor enhancing media may be sprayed, painted, flooded, or otherwise disposed around the exterior of uterus 240 to enhance the sensitivity of the capacitance sensors 210 or other sensing mechanism. For example, FIG. 4 illustrates a conductive gel 290 that may be sprayed or painted onto the exterior of the mobilized uterus 240, which will increase the resolution of the capacitive sensors 210. Such a media 290 can be a conductive gel, such as a hypertonic saline gel. A similar conductive gel would enhance the resolution impedance sensors. In another variation, a magnetic sensitive material could be disposed around the uterus 240, which could increase the resolution of a magnetic sensor carried by the working end 112 of the resecting device 105. In another variation shown in FIG. 5, a mesh net 300 can be disposed around the uterus 240 for similar purposes. For example, a structure similar to that stretchable nylon stocking with conductive threads could be disposed around the uterus 240 to increase the sensitivity of a capacitance sensor 210, an impedance sensor, or a magnetic sensor.

In another variation, a source of illumination or light emitters may be disposed in one or more locations around the window 118 of the exterior sleeve 125. Such illumination or light emitters can be added to the device of FIG. 2 or can be used instead of capacitance sensors 210 or other sensors. The light emitters can be, for example, a distal end of one or more optical fibers, an LED source, or other source of visible illumination. It can be understood that the physician then can see the brightness of the light through the translucent uterine wall and understand the proximity of the cutting blade 126 to the wall surface.

In one variation, the controller 140 includes algorithms to modulate or terminate operation of the resecting device 105 when the capacitance sensors 210 or other sensor mechanism indicate the proximity of the cutting blade to the exterior of uterine wall 244. In another variation, the sensor system can provide warning signals to the position of the cutting blade in the form of aural, visual, or tactile signals.

By using the system and method described above, it can be understood that the laparoscopic hysterectomy can be performed without the risk of dispersing any potentially malignant tissue in the abdominal cavity 248. All resected tissue chips are maintained within the interior of the uterus 240, with the uterine wall itself functioning as a containment sac. The system and method can be performed with any type of resecting device, such as a mechanical cutter, as shown herein, in which a blade can cut by rotation, reciprocation or both. In other variations, the resecting device may be an RF device, ultrasound device, laser device, microwave device, resistive heat device, or the like.

Figure 12:
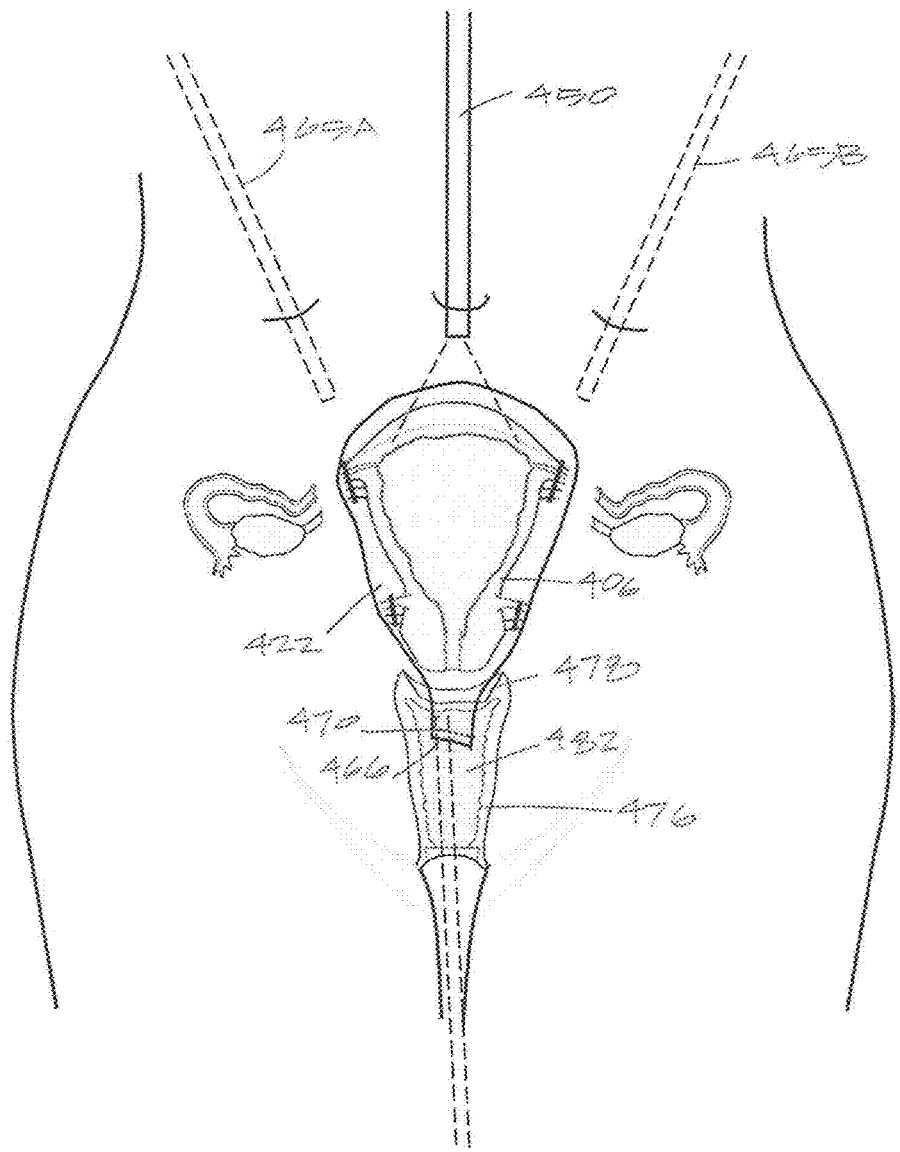
FIG. 12 is a subsequent step where the reduced-volume uterus is entirely contained in the containment sac.
Figure 13:
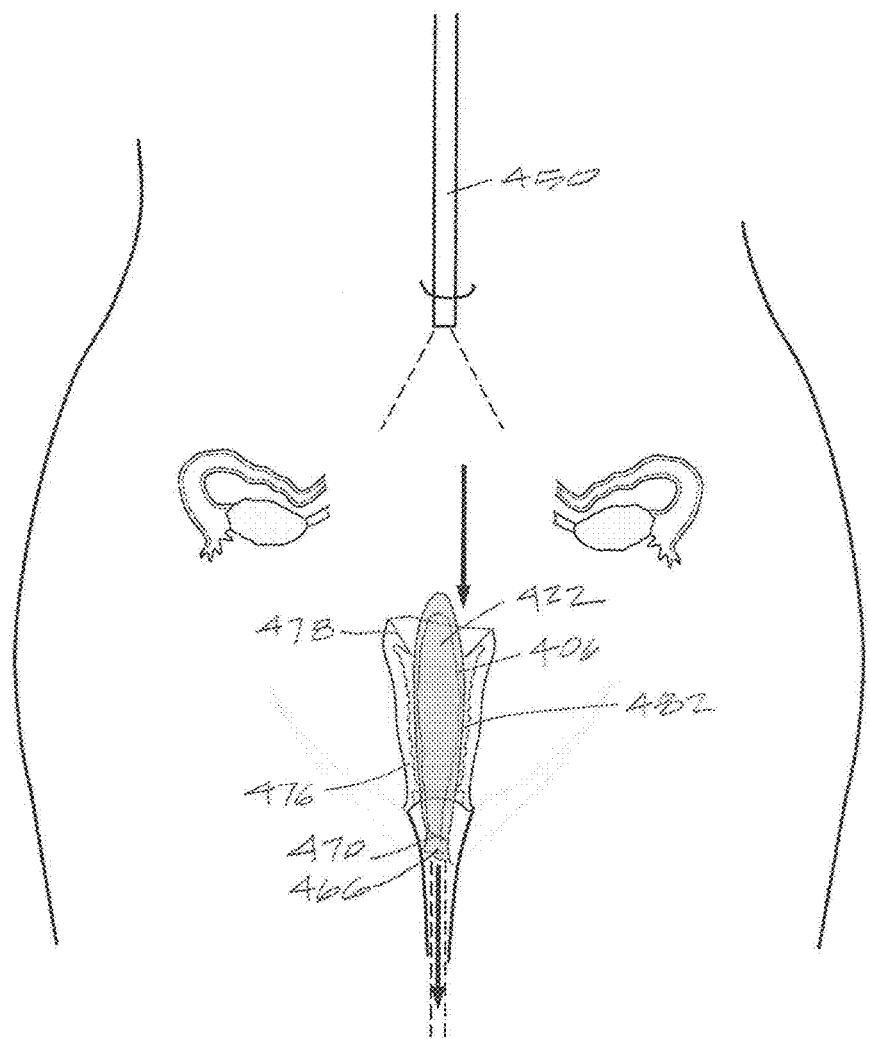
FIG. 13 shows the containment sac with the uterus in a collapsed condition being withdrawn through the patient's vagina.
Figure 14:
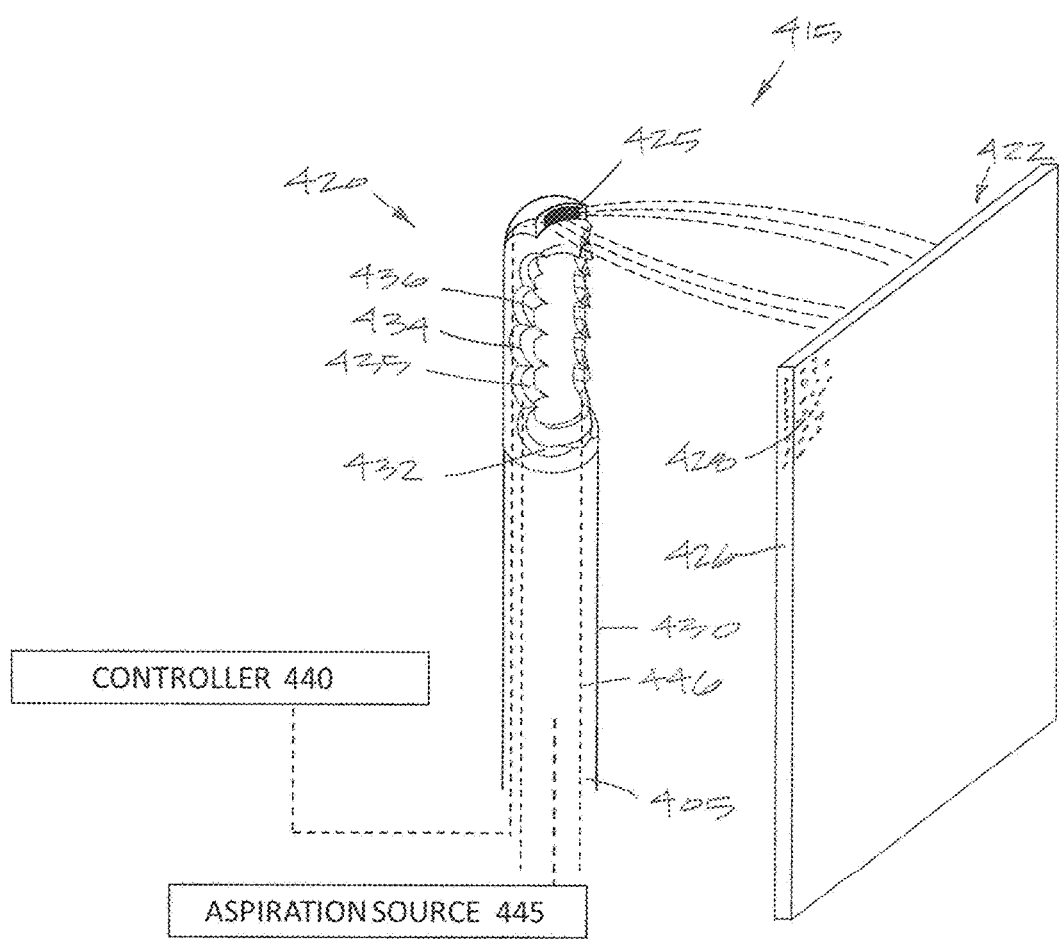
FIG. 14 is an enlarged schematic view of the sensor system, which comprises a first component or sensor carried on the resecting device and a second component of the sensor system comprising a sensor-responsive material carried in a wall of the containment sac.

Now referring to FIGS. 6 to 13, another variation of a system 400 and method is shown for resecting uterine tissue 402 comprising endometrium and myometrium in a less invasive trans-vaginal hysterectomy. In FIGS. 8-13, a resecting device 405 again is used to resect such uterine tissue 402 from the interior of a uterus 406 and maintains the serosa 408 of the uterus as a containment structure to prevent potentially malignant tissue from entering the abdominal cavity 412 of a patient. Turning to FIG. 14, it can be seen that the method again uses a resecting device 405 and sensor system 415 for sensing the proximity of the working end 420 of the resecting device 405 to the exterior surface of the uterus 406 wherein a containment sac 422 contains or encloses at least a portion of the uterus. FIG. 14 further shows the resecting device 405 carries a sensor 425 that comprises a first component of the sensor system 415 and a wall 426 of the containment sac 422 carries a sensor-responsive material, such as a ferromagnetic material 428, that comprises a cooperating second component of the sensor system 415. In one variation, referring to FIG. 14, the resecting device 405 is configured with an elongated shaft 430 having an outer sleeve 432 with an outer cutting window 434 and a motor-driven inner sleeve or cutting member 435 with an inner cutting member window 436 that resects tissue as it rotates and/or oscillates axially. A controller 440 controls the motor drive that actuates the cutting member 435. An aspiration source 445 is coupled to a passageway 446 in the cutting member 435 to extract resected tissue chips. The sensor system 415 is coupled to the controller 440 to control the actuation, or rotational speed, of the cutting member 435 in response to signals from the sensor system 415 that indicate the proximity of the cutting member 435 from the serosa 408 of the uterus 406 and containment sac 422.

Figure 6:
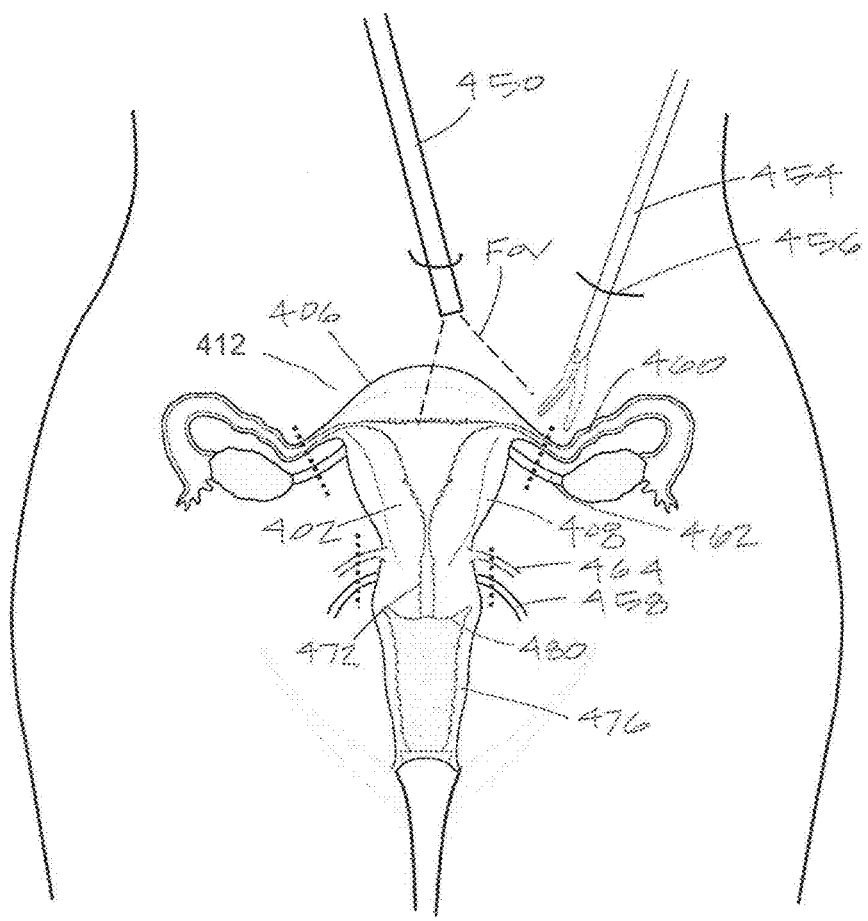
FIG. 6 is a schematic view of a first step in a transvaginal hysterectomy method corresponding to the invention where the surgeon is mobilizing the patient's uterus with laparoscopic tools.

Now turning to FIG. 6 and a method of the invention, an initial step of the tissue resection method includes a laparoscopic approach to mobilize the patient's uterus 406. An endoscope 450 is typically introduced centrally in the abdominal wall, followed by insufflation of the abdominal cavity 412, wherein the endoscope provides a suitable field of view FOV as shown in FIG. 6. At least one tool 454, such as a cutting instrument, is introduced through a port 456 in the abdominal wall, wherein a typical instrument is a dual-function bipolar device for cutting and sealing tissue. To mobilize the uterus 406, the surgeon ligates and ties the uterosacral ligaments 458, fallopian tubes 460, round ligaments 462, and supporting tissues around the uterus. The uterine arteries 464 are transected and sealed. The exterior of the uterus 406 is bluntly dissected away from adjacent organs.

Figure 7:
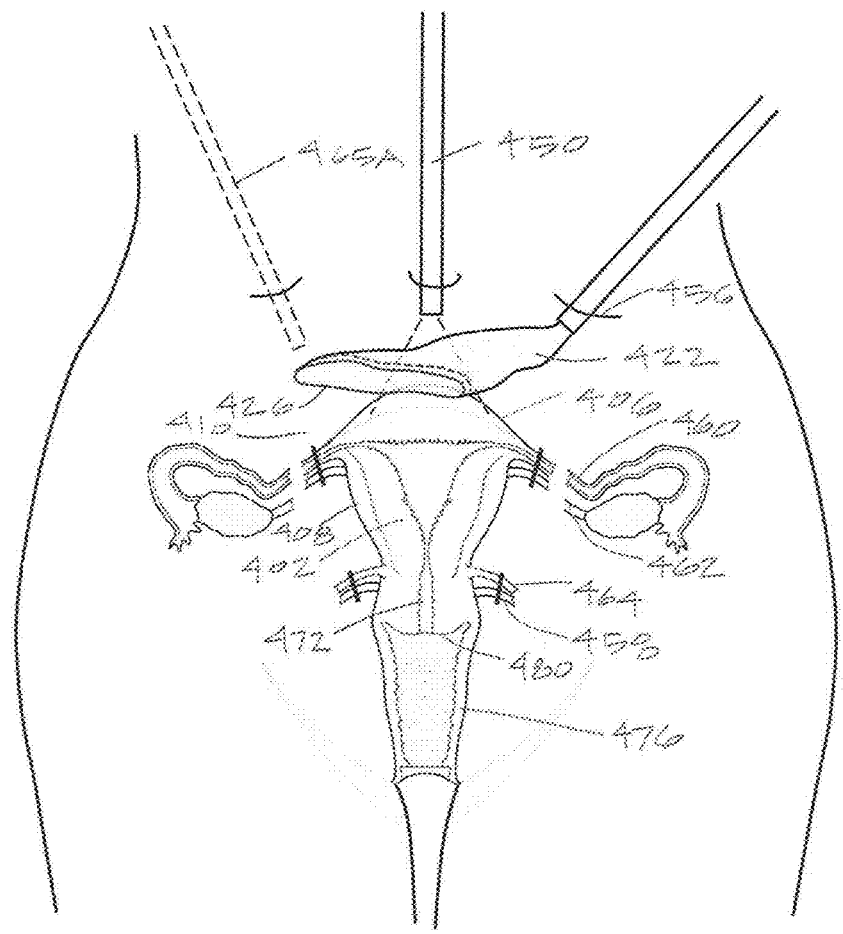
FIG. 7 is a subsequent step of the method wherein a containment sac is introduced into the patient's abdominal cavity for containing the mobilized portion of the uterus, wherein the cervix and its connection to the patient's vagina are still intact.
Figure 8:
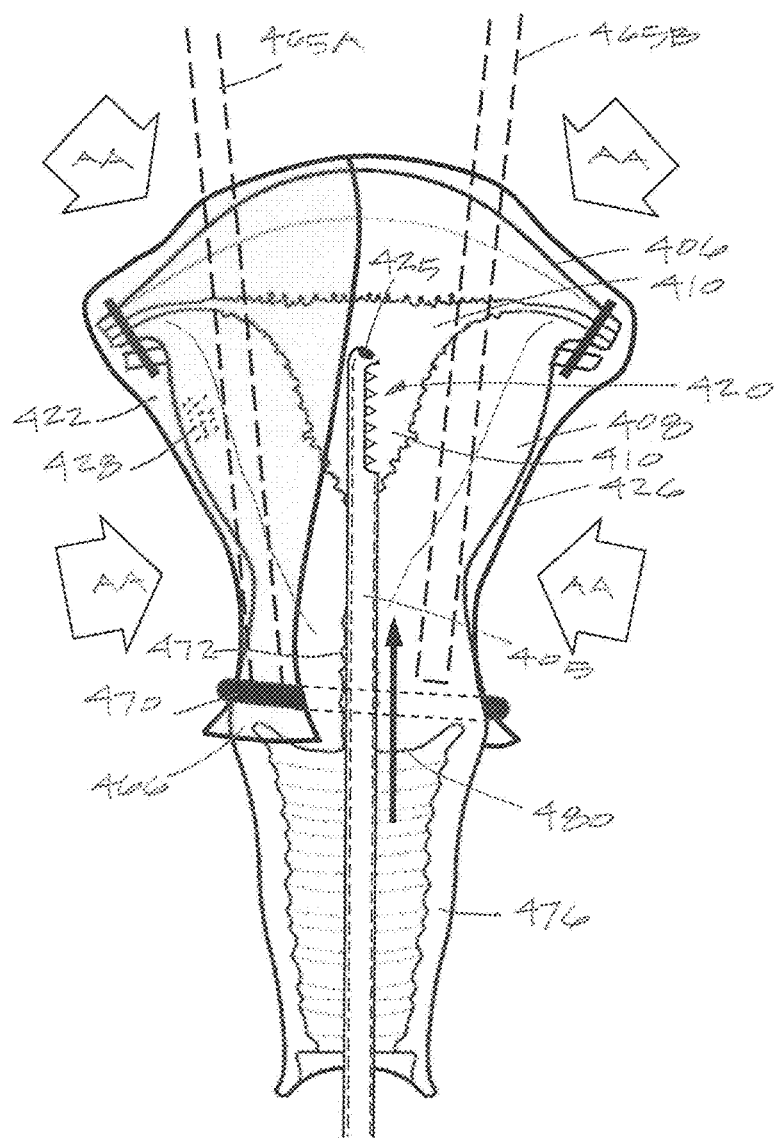
FIG. 8 is a subsequent step in an enlarged view with the mobilized uterus being disposed in the containment sac in cut-away view with insufflation pressures collapsing the sac on the uterus, and further showing a resecting device being introduced trans-vaginally into the uterine cavity.

FIG. 7 shows the containment sac 422 with a thin, flexible polymeric wall 426 being introduced through an abdominal port 456 wherein the sac is adapted to be positioned over and around the partly mobilized uterus 406. FIG. 8 is an enlarged view of the uterus 406 with the containment sac 422 disposed around the mobilized portion of the uterus, wherein it would typically include first and second tools 465A, 465B being used to close the inferior portion 466 of the sac 422 around the exterior of the uterus 406 with a closure member 470. In FIG. 8, the arrows AA indicate insufflation pressure being adapted to compress the walls 426 off the containment sac 422 against the uterus 406 before the closure member 470 is tightened to close the sac 422 around the uterus 406. In other variations, negative pressure may be introduced with an aspiration tool between the sac 422 and uterus 406 to collapse the flexible sac wall 426 tightly against the outer surface of the uterus.

FIG. 8 further shows the resecting device 405 being introduced through the patient's cervical canal 472 into the uterine cavity 410 to resect and remove uterine tissue. In a variation shown in FIGS. 8, 9, and 14, the working end 420 of the resecting device 405 carries the first component of the sensor system 415 (FIG. 14) comprising a magnetic proximity sensor 425 that cooperates with the second component of the sensor system 415 comprising the ferromagnetic material 428 in the wall 426 of the containment sac 422. As described previously, the sensor system 415 is coupled to the controller 440, and a control algorithm determines when the sensor 425 at working end 420 and cutting member 435 of the resecting device 405 reaches a predetermined distance from the wall of the containment sac 422 which is collapsed onto the outer surface of the uterus 406 (FIG. 14). The predetermined distance can be 10 mm, 8 mm, 6 mm, 4 mm, 2 mm or any selected distance that provides a desired degree of protection. The controller 440 is configured to provide a warning signal and/or de-activate rotation or other movement of the cutting member 435 when the predetermined distance is reached.

Figure 9:
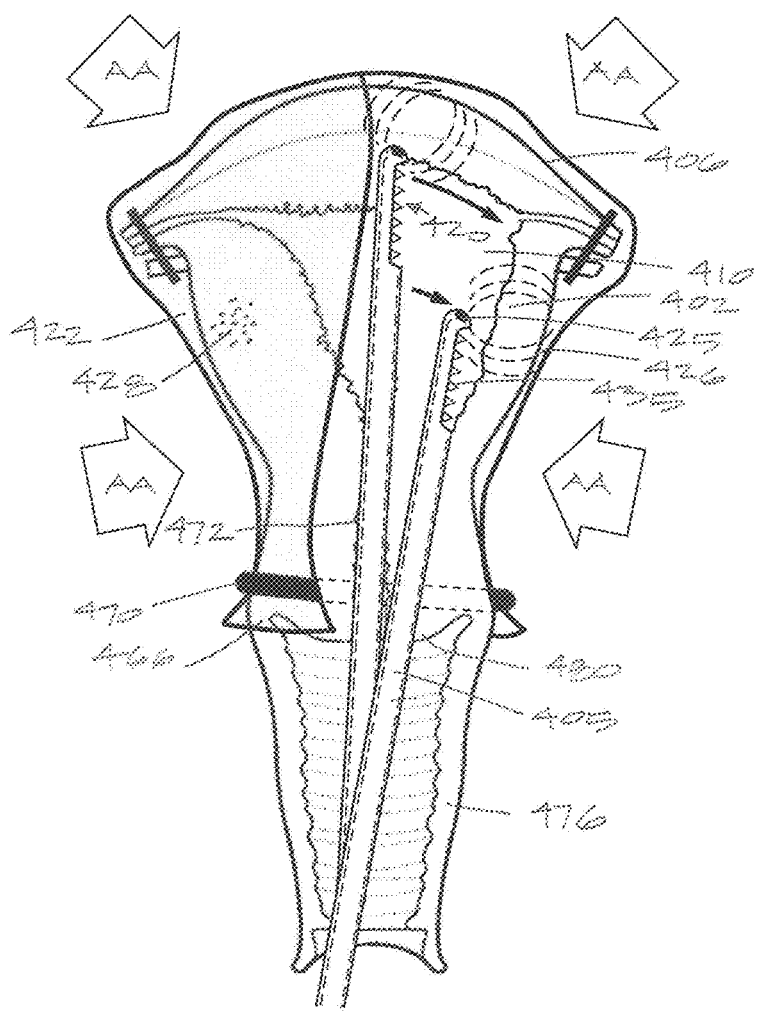
FIG. 9 is a subsequent step of the method where the motor-driven resecting device is moved axially, rotationally, and angularly to resect a substantial volume of tissue from the interior of the uterus with a sensor system detecting when the cutting member approaches the outer surface of the uterus and the wall of the containment sac to prevent perforation of the uterus.
Figure 10:
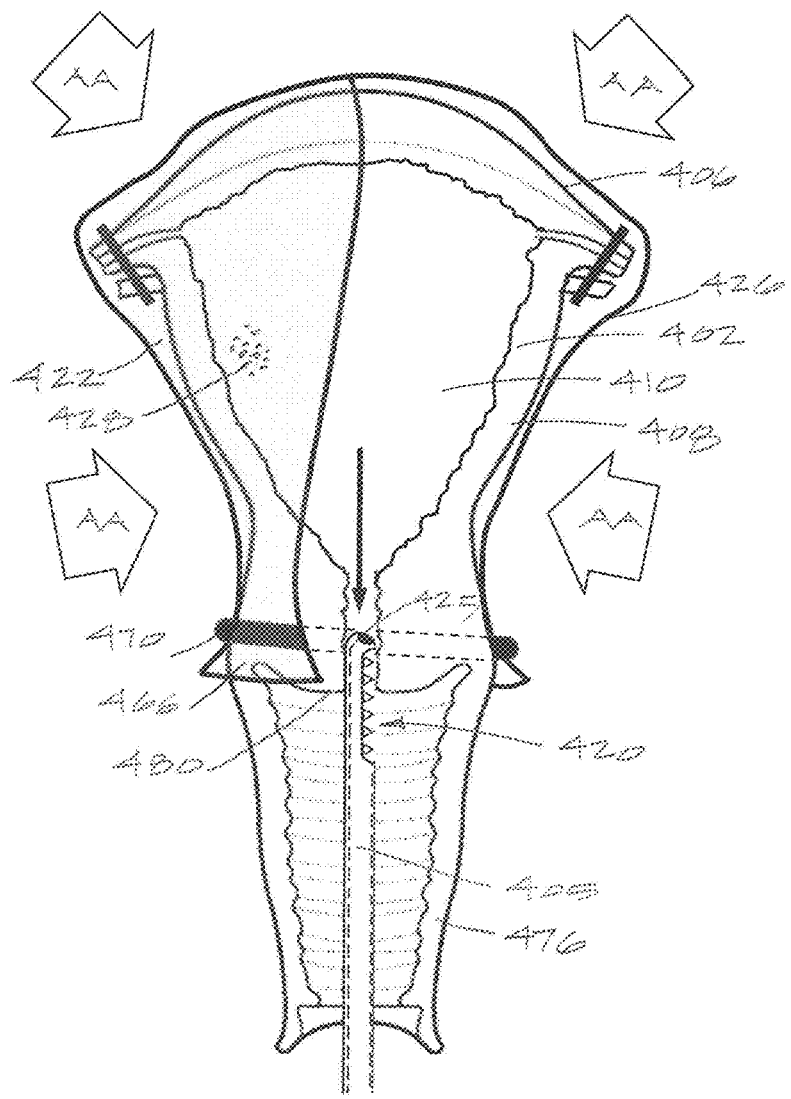
FIG. 10 is a subsequent step where a substantial volume of the uterine tissue has been removed, and the resecting device is being withdrawn.

In FIG. 9, it can be seen that the working end 420 of the resecting device 405 has been moved axially, rotationally, and angularly to resect a substantial volume of endometrium 402 from the interior of the uterus 406 without perforating the serosa 408. FIG. 10 next shows the subsequent step, where uterine tissue or endometrium 402 is resected from both sides of uterine cavity 410, leaving the serosa 408 and a thin layer of the endometrium 402 intact. In this example, the intact serosa 408 prevents any potentially malignant material from escaping into the abdominal cavity 410. FIG. 10 further shows the working end 420 of the resecting device 405 being withdrawn from the uterine cavity 410.

FIGS. 8, 9, and 14 further show the resecting device 405 carrying the proximity sensor in the form of a magnetic or Hall effect sensor 425, which can measure the presence or absence of a magnetic field of the ferromagnetic material 428 in the wall 426 of the containment sac 422. In this variation, the sensor 425 is disposed at a distal tip of the working end 420 and faces generally perpendicular to the cutting windows 434 and 436. The ferromagnetic material 428 can comprise particles, filaments, wires, or any other suitable ferromagnetic elements. It should be appreciated that one or more sensors may be positioned around or adjacent to the cutting windows 434 and 436. Referring to FIG. 14, it can be understood that the sensor signals will vary as the sensor 425 moves into closer proximity to the wall 426 of sac 422, wherein the controller 440 can determine when the cutting member 435 reaches a pre-selected distance from the sac 422 at the exterior of the uterus 406. As can be understood, the wall of the uterus is not shown in FIG. 14 but is adjacent to the sac wall 426. In a variation, the controller 440 can provide signals to a display to continuously display the distance of cutting number 435 from the wall 426 of the containment sac 422, as well as providing alarms.

In another variation, an electrical source can be coupled to a conductive material in the wall 426 of the sac 422 to provide a magnetic field. Other types of proximity sensors are known in the art and can be used. For example, a capacitive proximity sensor, as known in the art, can be used that detects the presence or proximity of the sensor to a targeted material in the containment sac 422 using a capacitive sensing effect. In another variation, an eddy current proximity sensor or switch can be used that detects the proximity or presence of a targeted material in the sac 422 by sensing the magnetic fields generated by a reference coil. In another variation, an inductive proximity sensor can be used to detect the presence or absence of a targeted material in the containment sac 422 at a critical distance. Various types of electronic proximity sensors, as described above, can be acquired from NVE Corporation, 11409 Valley View Road, Eden Prairie, MN 55344. In other variations, a photoelectric or optical sensor system can be used where an LED emitter and sensor can sense light emissions reflected from the wall of the sac 422. In another variation, an ultrasound transducer can be carried by the resecting device that can sense reflected sound waves that are reflected off the wall of the containment sac 422.

Figure 11:
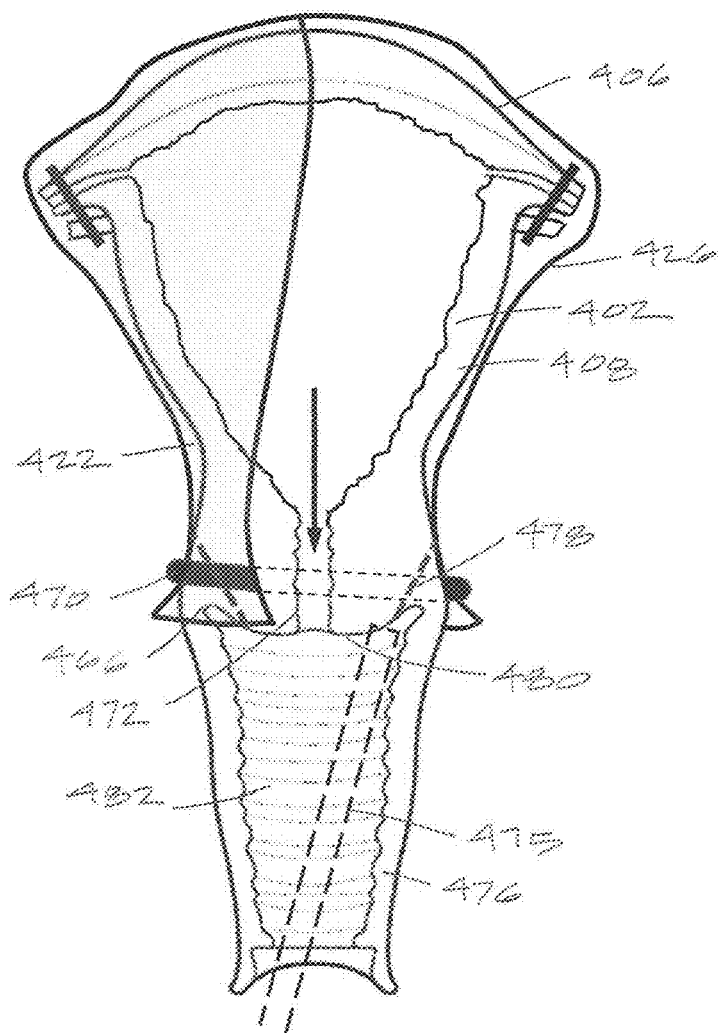
FIG. 11 is another step where a cutting tool is introduced trans-vaginally to make a circumferential incision to separate the cervix and uterus from the vagina.

FIG. 11 shows a subsequent step of the method wherein a cutting instrument 475 such as a scalpel, is introduced through the patient's vagina 476 to make a circumferential incision 478 around the cervix 480 to separate the cervix from the wall of the vaginal canal 482. FIG. 12 next illustrates the closure member 470 of the containment sac 422 being tightened or closed at the inferior end 466 of the sac 422 to surround the mobilized uterus 406 for removal trans-vaginally. FIG. 13 shows the 422 sac and reduced-volume uterus 406 being collapsed and removed through the patient's vaginal canal 482. Subsequent steps of such a vaginal hysterectomy are known and include closure of the vaginal vault and often suturing the uterosacral ligaments to the upper region of the vagina to prevent prolapse of the vaginal vault (not shown).

Figure 15A:
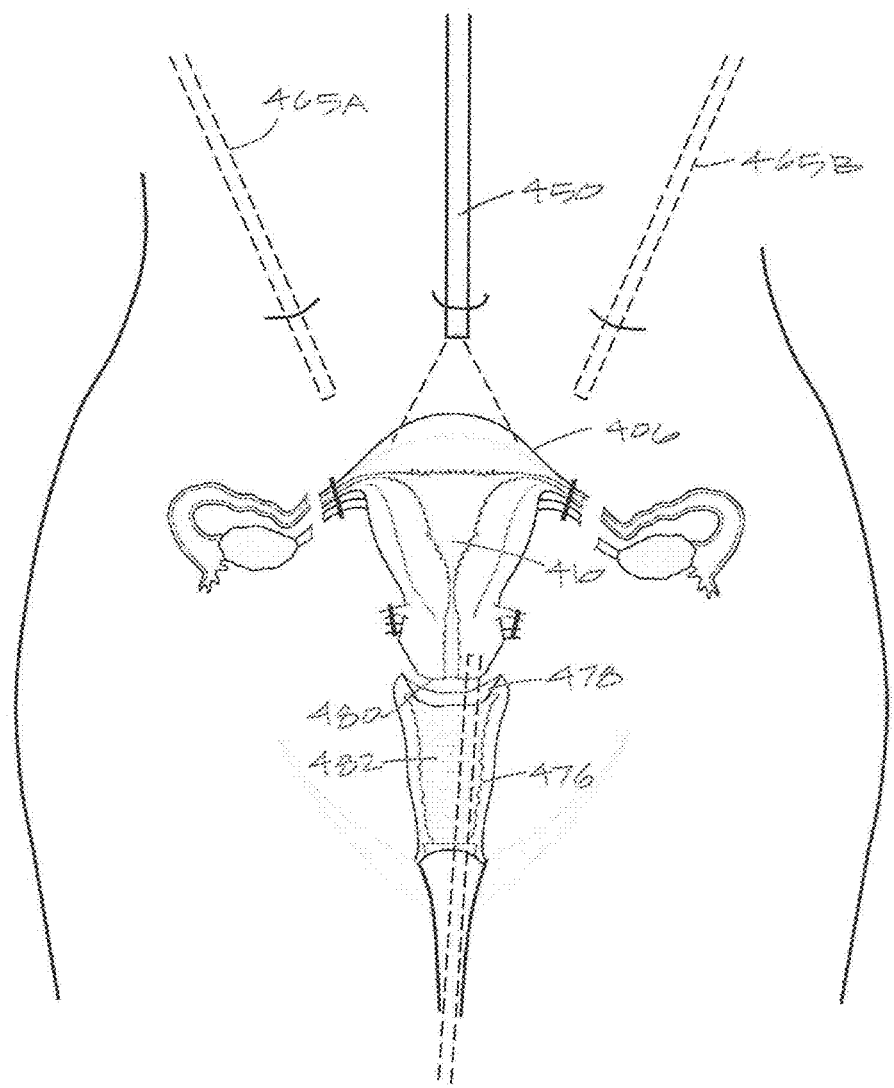
FIG. 15A is another variation of a trans-vaginal hysterectomy procedure similar to that of FIGS. 6 to 3 where the patient's uterus is entirely mobilized, including the circumferential incision separating the cervix from the patient's vagina in a first step.
Figure 15B:
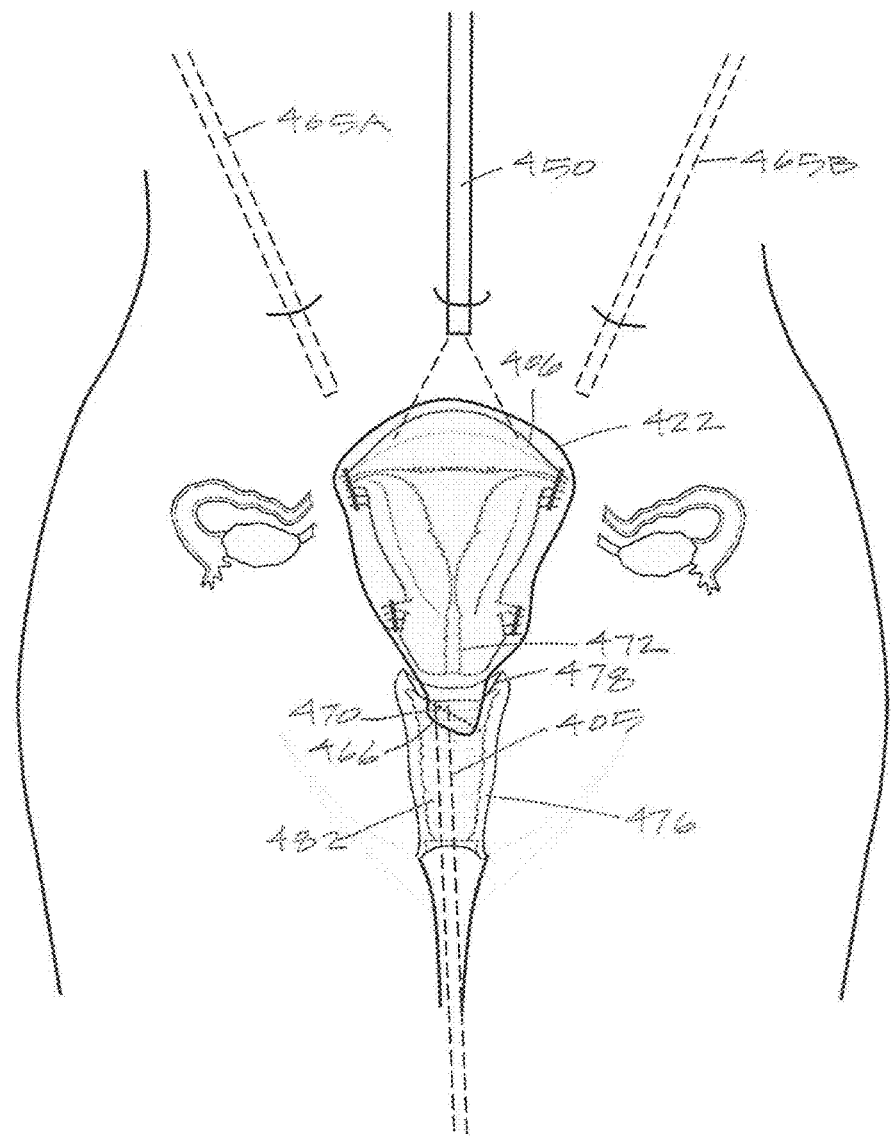
FIG. 15B is a subsequent step where in the uterus is entirely contained within the containment sac and prepared for introduction of a resecting device into the uterine cavity to remove a substantial tissue volume.
Figure 15C:
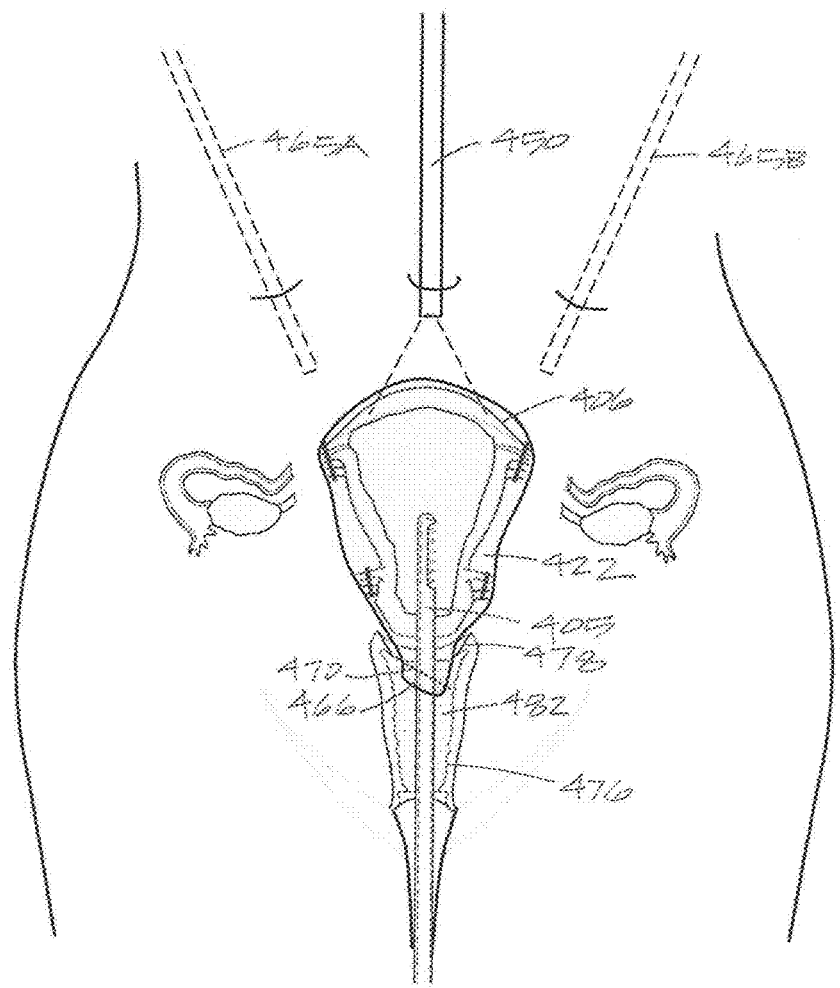
FIG. 15C shows the uterus after a substantial volume of uterine tissue has been removed from the uterus while contained within the containment sac with the sensor system operating as shown in FIGS. 9 and 14.

FIGS. 15A and 15B illustrate another variation of a tissue resection method that is similar to the previously described method of FIGS. 6-13. In the variation shown in FIG. 15A, the surgeon entirely mobilizes the patient's uterus 406 using a transvaginal approach before resecting and removing tissue from the interior of the uterine cavity 410. In FIG. 15A, the circumferential incision 478 at the cervix 480 entirely immobilizes the uterus 406 and FIG. 15B shows the containment sac 422 positioned around the uterus and closed except for an access through the open end of the sac 422 to allow the resecting device 405 to be introduced the cervical canal 472 to resect tissue from the uterus 406. FIG. 15C then shows the resecting device 405 having removed a substantial volume of uterine tissue from interior of the uterus. In all other aspects, the method of FIGS. 15A-15B are similar to the steps shown in FIGS. 6 to 13. FIG. 15B, wherein the resecting device removed tissue with the sensor system functioning as described above.

Figure 16:
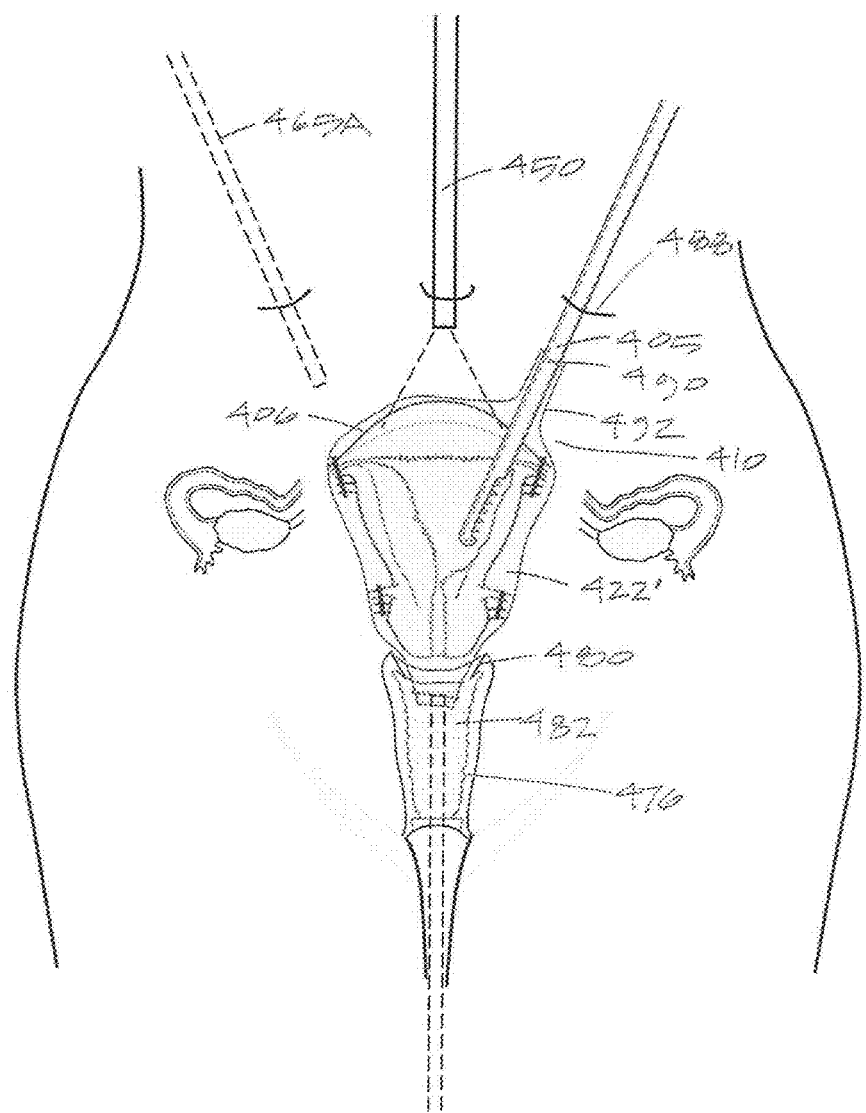
FIG. 16 illustrates an alternative method wherein the uterus is again entirely mobilized and contained within a containment sac as described in FIGS. 15A-15C, however, the resecting device is introduced through an abdominal port to remove a substantial volume of tissue from the interior of the uterus.

FIG. 16 shows another variation of a method of resecting tissue which is similar to that of FIGS. 15A and 15B above. In this variation, the uterus 406 again is completely mobilized and disposed in a containment sac 422'. However, in this variation, the resecting device 405 is introduced laparoscopically through a port 488 in the abdominal wall and a resection port 490 in an extending wall portion 492 of the sac 422'. The extending wall portion 492 and resection port 490 may be disposed in the uterine cavity 410 or comprise an elongated portion of the sac 422' extending outward of the port 488 and the abdominal wall. In this variation, following resection of uterine tissue, the reduced-volume uterus 406 can be removed trans-vaginally or can be removed through a port or incision in the abdominal wall.

Although particular embodiments of the present invention have been described above in detail, it will be understood that this description is merely for purposes of illustration, and the above description of the invention is not exhaustive. Specific features of the invention are shown in some drawings and not in others, and this is for convenience only, and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

All references, including publications, patent applications, and patents, cited herein are hereby incorporated by reference to the same extent as if each reference were individually and specifically indicated to be incorporated by reference and were set forth in its entirety herein.

What is claimed is:

1. A method of resecting tissue, comprising:

introducing a working end of a resecting device into an interior of a uterus of a patient, wherein the working end carries a cutter that is motor driven and a first component of a sensor system;

positioning a stretchable substrate around an outer surface of the uterus, wherein the stretchable substrate carries a second component of the sensor system;

wherein the first component and the second component of the sensor system are coupled to a controller configured to provide a signal when the cutter approaches a predetermined distance from the stretchable substrate around the outer surface of the uterus; and resecting tissue with the cutter to remove a substantial volume of tissue from within the interior of the uterus and responsive to the signal, preventing the cutter from perforating the outer surface of the uterus to thereby prevent dispersion of potentially malignant tissue from the interior of the uterus.

2. The method of claim 1 wherein the signal causes de-activation of the cutter to stop resecting tissue.

3. The method of claim 1 wherein the signal consists of at least one of aural, visible or tactile signals to warn an operator to stop resecting tissue.

4. The method of claim 1 wherein positioning the stretchable substrate is preceded by mobilizing at least a portion of the uterus superior to a cervicovaginal intersection.

5. The method of claim 4 wherein positioning the stretchable substrate comprises disposing the substrate in a form of a sac around a mobilized portion of the uterus.

6. The method of claim 5 further comprising detaching the uterus from a body of the patient with a circumferential incision around a cervix at the cervicovaginal intersection and removing the uterus when detached within the sac from a body of the patient.

7. The method of claim 6 wherein the uterus, when detached, and sac are removed from the body of the patient through a transvaginal access.

8. The method of claim 6 wherein the uterus, when detached, and sac are removed from the body of the patient through a laparoscopic access.

9. The method of claim 4 wherein mobilizing at least a portion of the uterus is performed with instruments introduced through at least one of a transvaginal access and a laparoscopic access.

10. The method of claim 5 further comprising insufflating an abdominal cavity to cause the sac to approximate around the outer surface of the uterus.

11. The method of claim 1 wherein the first component of the sensor system comprises a Hall effect or magnetic sensor.

12. The method of claim 11 wherein the second component of the sensor system comprises a ferromagnetic element.

13. The method of claim 1 wherein the first component of the sensor system comprises an inductive or eddy current sensor.

14. The method of claim 13 wherein the second component of the sensor system comprises a ferrous element.

15. The method of claim 1 wherein the first component of the sensor system comprises a capacitive or inductive sensor.

16. The method of claim 1 wherein the first component of the sensor system comprises a light emitting element.

17. The method of claim 1 wherein the first component of the sensor system comprises an ultrasound transducer.

18. The method of claim 5 wherein the sac has an open end for receiving the uterus, when mobilized, including means for closing the open end around the uterus, when mobilized.

19. The method of claim 5 wherein the sac has a port for receiving the resecting device introduced laparoscopically.

20. The method of claim 4 wherein the uterus is mobilized with tools introduced through a transvaginal access.

21. The method of claim 4 wherein the uterus is mobilized with tools introduced through a laparoscopic access.

* * * * *